(12) United States Patent  
Iaizzo et al.

(10) Patent No.: US 8,019,437 B2
(45) Date of Patent: Sep. 13, 2011

(54) LEAD FIXATION MEANS

(75) Inventors: Paul A. Iaizzo, White Bear Lake, MN (US); Timothy G. Laske, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/772,989

(22) Filed: Feb. 5, 2004

(65) Prior Publication Data

US 2005/0177220 A1  Aug. 11, 2005

(51) Int. Cl.
*A61N 1/04* (2006.01)
(52) U.S. Cl. ......... 607/116; 607/126; 607/127; 607/130
(58) Field of Classification Search .................. 607/116, 607/119, 122, 126, 129, 130, 127
See application file for complete search history.

(56) References Cited

U.S. PATENT DOCUMENTS

| | | | | |
|---|---|---|---|---|
| 4,282,886 A | * | 8/1981 | King | 607/130 |
| 4,768,523 A | * | 9/1988 | Cahalan et al. | 607/116 |
| 5,383,899 A | * | 1/1995 | Hammerslag | 606/214 |
| 5,571,161 A | * | 11/1996 | Starksen | 607/122 |
| 5,935,124 A | * | 8/1999 | Klumb et al. | 606/42 |
| 6,251,115 B1 | * | 6/2001 | Williams et al. | 606/108 |
| 6,324,435 B1 | * | 11/2001 | Shchervinsky et al. | 607/152 |
| 6,341,230 B1 | * | 1/2002 | Koike et al. | 600/392 |
| 6,463,335 B1 | * | 10/2002 | Munch et al. | 607/129 |
| 6,475,179 B1 | * | 11/2002 | Wang et al. | 604/41 |
| 6,516,230 B2 | * | 2/2003 | Williams et al. | 607/116 |
| 6,602,241 B2 | * | 8/2003 | Makower et al. | 604/509 |
| 6,666,844 B1 | * | 12/2003 | Igo et al. | 604/115 |
| 6,718,212 B2 | * | 4/2004 | Parry et al. | 607/130 |
| 6,726,920 B1 | * | 4/2004 | Theeuwes et al. | 424/423 |
| 6,931,286 B2 | * | 8/2005 | Sigg et al. | 607/120 |
| 7,099,718 B1 | * | 8/2006 | Thacker et al. | 607/117 |

FOREIGN PATENT DOCUMENTS

DE  2453840 A1 * 5/1976
DE  24 53 840  1/1978

OTHER PUBLICATIONS

Translation of DE 2453840.*
Hansen, G.L. et al., "Assessing Wound Severity With Color and Infrared Imaging of Reactive Hyperemia," *Wound Repair and Regeneration*, p. 386-392 (Jul.-Sep. 1996).

* cited by examiner

*Primary Examiner* — Eric D. Bertram
(74) *Attorney, Agent, or Firm* — Carol F. Barry

(57) ABSTRACT

A medical electrical lead includes a glue segment to adhere the lead to a treatment site. The glue segment, which may be disposed within a tip electrode of the lead, includes tissue adhesive which may encapsulated within a capsule.

17 Claims, 6 Drawing Sheets

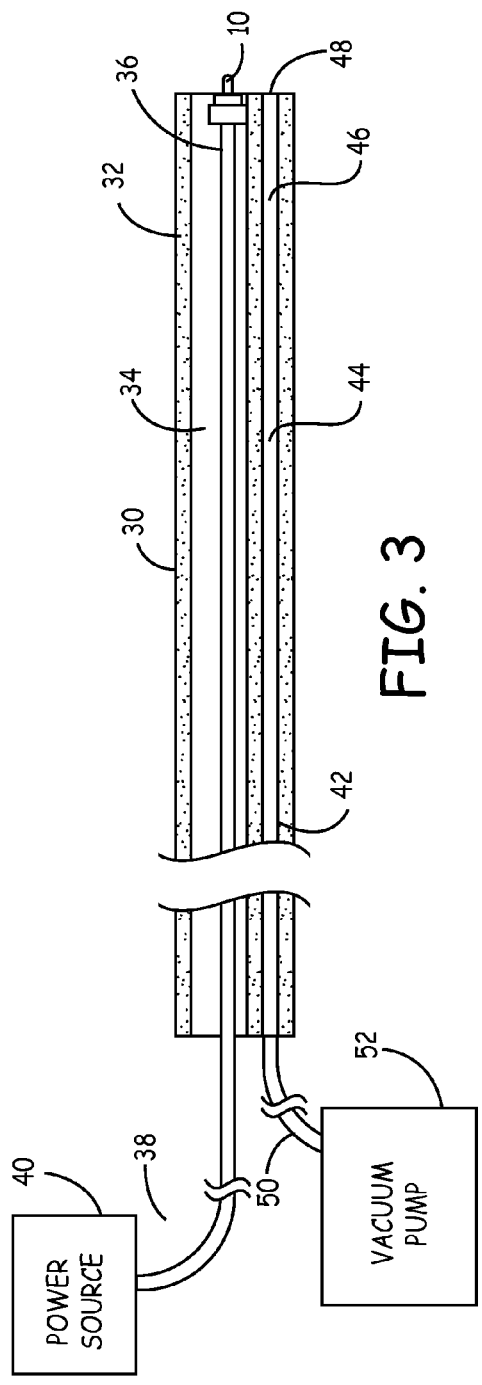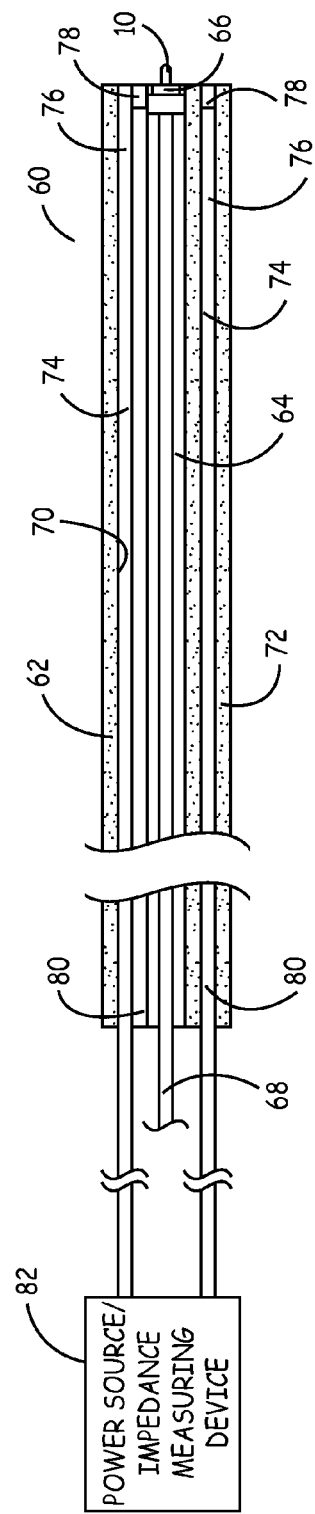

LEAD FIXATION MEANS

TECHNICAL FIELD

The present invention generally relates to leads for implantable medical devices, and more particularly to medical leads that are securely affixed to a tissue of an animal or human.

BACKGROUND

An implantable medical device (IMD) is a device placed inside a body to monitor certain physiological signals and provide therapy to an organ or tissue in response to the physiological signals. The IMD may be, for example, but not by way of limitation, a pacemaker. For convenience, all types of implantable medical devices will be referred to herein as IMDs, it being understood that the term, unless otherwise indicated, is inclusive of an implantable device capable of administering any of a number of therapies to the heart or other organs or other tissue of the patient. For convenience the present invention will be described in terms of a cardiac pacemaker lead, it being understood that the invention also may have applicability to other types of leads, which deliver therapy to alternates sites and according to other modalities known to those skilled in the art.

Typically, leads are coupled or attached to heart tissue using an a helix-coil that is wound or "screwed" into the tissue or using tined protrusions which catch in tissue in proximity to an implant site. In some cases, helix-coil electrodes and tines may not necessarily result in a secure attachment, for example if the tissue does not facilitate such attachment or if a lead is of such a small size to prevent secure attachment. Accordingly, it is desirable to provide improved means for securely attaching a medical lead to tissue of a human or animal.

BRIEF DESCRIPTION OF THE DRAWINGS

The present invention will hereinafter be described in conjunction with the following drawing figures, wherein like numerals denote like elements.

FIG. 3 is a cross-sectional view of the medical lead of FIG. 1 disposed within a suction catheter;

FIG. 4 is a cross-sectional view of the medical lead of FIG. 1 disposed within a mapping catheter;

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

Figure 1:
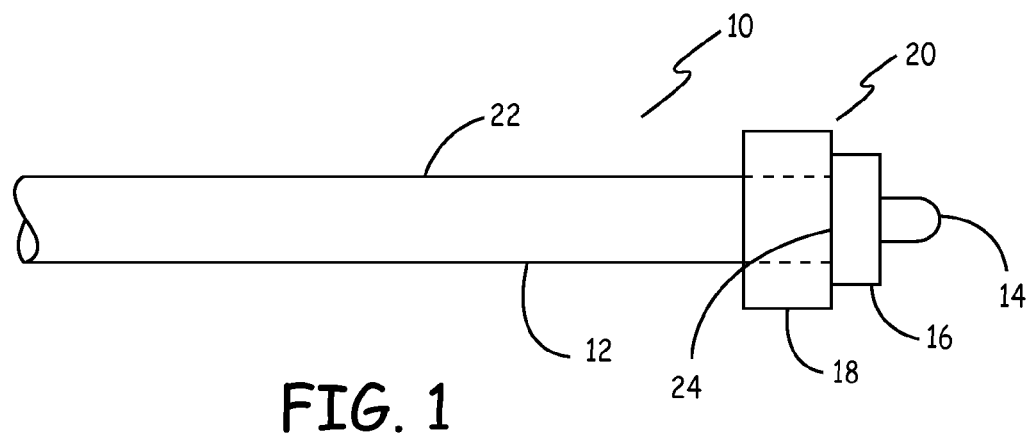
FIG. 1 is a plan view of a portion of a medical lead in accordance with one exemplary embodiment of the present invention.

FIG. 1 is a representation of a medical lead 10, in accordance with an exemplary embodiment of the present invention, which is used to securely couple an implantable medical device to an organ or other tissue of a human or animal body (hereinafter, collectively "tissue"). Lead 10 includes an elongated insulative lead body 12 fabricated, for example, of silicone rubber, polyurethane or other biocompatible elastomer. At a distal end 20 of lead 10 is carried a tip electrode 14, which is coupled to a conductor (not shown) within lead body 12. In this exemplary embodiment of the invention, tip electrode 14 may correspond to any conventionally available epicardial and/or endocardial pacing and/or defibrillation electrodes that are to be affixed to a location of the heart for sensing or treatment (hereinafter, "the treatment site"). While lead 10 is illustrated in FIG. 1 having only one electrode, it will be appreciated that lead 10 may include any number and type of electrodes suitable for a desired treatment and/or sensing application.

Lead 10 further includes a glue segment 16. Glue segment 16 includes any conventionally available tissue adhesive or surgical sealant (hereinafter "tissue glue"), such as n-butyl cyanoacrylate or a biologic adhesive such as fibrin glue. According to one embodiment, glue segment 16 includes a tissue glue that cures upon contact with moisture, such as upon contact with water or blood. Examples of commercially available tissue glues suitable for use in the present invention include INDERMIL™, marketed by the Kendall Company of Mansfield, Mass., VETBOND®, marketed by 3M of St. Paul, Minn., NEXABAND®, marketed by Closure Medical Corporation of Raleigh, N.C. and Histocryl Blue™ marketed by Sherwood-Davis & Geck of St. Louis, Mo. The tissue glues may be removed from a treatment site by using any suitable solvent, such as, for example, dimethyl sulfoxide ("DMSO") and acetone. Glue segment 16 includes a tissue adhesive of any suitable consistency, such as a liquid or gel consistency. According to one embodiment, glue segment 16 includes tissue adhesive having a gel consistency so that it may maintain a desired shape. In one exemplary embodiment, illustrated in FIG. 1, glue segment 16 may have a disc or annular shape with tip electrode 14 positioned in the center of glue segment 16. In another exemplary embodiment, glue segment 16 is formed by one or more drops or "dots" of tissue glue positioned proximate to tip electrode 14. Alternatively, glue segment 16 may take on any other shape and size suitable to adhere lead 10 to tissue.

Glue segment 16 may be located at distal end 20 of lead 10 at any suitable point proximate to tip electrode 14 so that tip electrode 14 is able to make a suitable contact with the treatment site. In one exemplary embodiment of the invention, glue segment 16 is situated at the distal end of an outer longitudinal surface 22 of insulative lead body 12. In another exemplary embodiment of the invention, glue segment 16 is disposed on a distal surface 24 of lead body 12, which is perpendicular to longitudinal surface 22.

In another exemplary embodiment of the invention, medical lead 10 includes a guard 18, which may be formed of any suitable biocompatible material. Guard 18 may be positioned at any suitable location along lead 10 but preferably is positioned at or proximate to distal end 20 of lead 10. Glue segment 16 may be disposed on or adjacent guard 18. As described in more detail below, when a delivery catheter is used to deliver lead 10 to the treatment site, guard 18 serves to keep glue segment 16 from rubbing along a wall of the catheter. Accordingly, guard 18 may be of any suitable size or shape and may be disposed at any suitable location along lead body 12 for keeping glue segment 16 from contacting the catheter wall.

Figure 2:
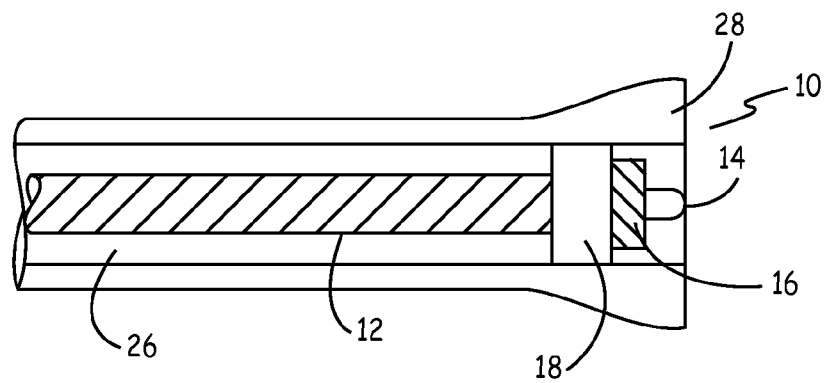
FIG. 2 is a cross-sectional view of the portion of the medical lead shown in FIG. 1 disposed within a delivery catheter.

FIG. 2 illustrates lead 10 positioned within a lumen 26 of a delivery catheter 28. Delivery catheter 28 may comprise any conventionally known medical catheter suitable for delivery of lead 10 to a treatment site. In one exemplary embodiment of the present invention, as described above, guard 18 has an annular shape and is sized such that its outer circumferential surface is proximate to an interior surface of catheter 28 surrounding lumen 26. In this manner, glue segment 16 does not contact the interior surface of catheter 28.

At least one class of tissue glues suitable for use in the present invention cures upon contact with moisture, such as blood, pericardial fluid, or water. Therefore, according to one exemplary embodiment of the invention, the delivery catheter 28 includes a suction catheter that aspirates from the treatment site excess blood, water or other fluid. It will be appreciated that the suction catheter may comprise any conventional suction catheter used in the medical industry. FIG. 3 illustrates a suction catheter 30 in accordance with one exemplary embodiment of the present invention. Suction catheter 30 includes a flexible body 32 within which is formed a first lumen 34. First lumen 34 is adapted to receive lead 10, as described above, and permits delivery of lead 10 to a treatment site. Lead 10 may include at a distal end 36 at least one electrode, such as a tip electrode, and may be connected at a proximal end 38 to a power source 40, such as a pacemaker or other implantable medical device. Suction catheter 30 further includes a second lumen 42 within which is seated a suction tube 44. Suction tube 44 has at a distal end 46 an opening 48 for receiving fluid from the treatment site. Suction tube 44 may be connected at a proximal end 50 to a vacuum pump 52 or other suitable device for creating a suction force at opening 48.

In accordance with an exemplary embodiment of the invention, a method for using a suction catheter to deliver a medical lead to a treatment site and to securely couple an implantable medical device to the treatment site of a heart will be described. For convenience, the method will be described with reference to suction catheter 30 and medical lead 10. However, it will be understood that the method may utilize any suitable suction catheter and any suitable embodiment of the medical lead of the present invention. Lead 10 may be secured to a selected treatment site, such as the myocardium of the heart, using suction catheter 30 by first inserting suction catheter 30 into a suitable blood vessel, such as a vein or artery, and urging suction catheter 30 through the blood vessel until a distal end of suction catheter 30 is positioned proximate to the myocardium. If not already connected, vacuum pump 52 may be connected for fluid communication with suction tube 44. Vacuum pump 52 then may be activated so that a suitable amount of fluid at the treatment site is removed through opening 48 of suction tube 44. After a suitable period of suction time, and/or after a suitable amount of fluid has been removed from the treatment site, lead 10 may be inserted into first lumen 34 and urged through suction catheter 30 until the electrode is proximate the myocardium. In an alternative embodiment of the invention, lead 10 may be urged through suction catheter 30 before activation of vacuum pump 52. Vacuum pump 52 then may be activated before lead 10 is secured to the treatment site to ensure that glue segment 16 makes suitable contact with the tissue (i.e., myocardium) at the treatment site.

Lead 10 then may be urged against the treatment site so that glue segment 16 contacts the treatment site and adheres thereto upon contact with moisture at the treatment site once vacuum pump 52 is deactivated. After suction catheter 30 is removed from the treatment site, leaving lead 10 securely fastened to the treatment site, an implantable medical device, such as a defibrillation unit or pacemaker, then may be suitably electrically connected to the proximal end of lead 10.

According to another exemplary embodiment of the invention, delivery catheter 28 includes a steering and/or mapping catheter having one or more sensors proximate a distal end of the catheter for producing signals that indicate the location of the sensor(s). Accordingly, the mapping catheter may be used to accurately position the electrode of lead 10 at the optimal treatment site. It will be appreciated that the steering and/or mapping catheter may comprise any conventional steering and/or mapping catheter used in the medical industry. FIG. 4 illustrates a mapping catheter 60 in accordance with one exemplary embodiment of the present invention. Mapping catheter 60 includes a flexible body 62 including a first lumen 64. First lumen 64 is adapted to receive lead 10, as described above, and permits delivery of lead 10 to a treatment site. Lead 10 may include at a distal end 66 at least one electrode, such as a tip electrode, and may be connected at a proximal end 68 to a power source (not shown), such as a pacemaker or other implantable medical device. Mapping catheter 60 further includes a second lumen 70 and a third lumen 72 within which are seated sensors circuits 74. As illustrated in FIG. 4, sensors circuits 74 include at distal ends 76 one or more electrical contacts 78, such as bipolar contacts, through which an electrical current may be emitted and received; further, sensor circuits 74 are connected at proximal ends 80 to a power source and impedance measuring device(s) 82 that is configured to send an electric potential through electrical contacts 78 and measure the change in impedance when electrical contacts 78 contact the treatment site surface. Electrical contacts 78 also may be configured to exhibit additional functions. For example, electrical contacts 78 may be configured to sense intrinsic electrical activity of the heart in order to optimize the location of the treatment site.

In accordance with an exemplary embodiment of the invention, a method for using a mapping catheter to deliver a medical lead to a treatment site and to securely couple an implantable medical device to the treatment site of a heart will be described. For convenience, the method will be described with reference to mapping catheter 60 and medical lead 10. However, it will be understood that the method may utilize any suitable mapping or steering catheter and any suitable embodiment of the medical lead of the present invention. Lead 10 may be secured to a selected treatment site, such as the myocardium of the heart, using mapping catheter 60 by first inserting mapping catheter 60 into a suitable blood vessel and urging mapping catheter 60 through the blood vessel until a distal end of mapping catheter 60 is positioned proximate to the myocardium. As mapping catheter 60 is urged through the blood vessel, the power source/impedance measuring device 82 may transmit an electric potential through electrical contacts 78 and the impedance between the electrical contacts 78 may be measured. When a suitable change in the impedance between electrical contacts 78 indicates that the distal end of the mapping catheter is proximate to the treatment site, lead 10 may be inserted into first lumen 64 and urged through mapping catheter 60 until distal end 66 of lead 10 is proximate the treatment site. Lead 10 then may be urged against the treatment site so that glue segment 16 contacts the treatment site and adheres thereto upon contact with moisture at the treatment site. After adherence of lead 10 to the treatment site, mapping catheter 60 may be removed from the treatment site and the blood vessel, leaving lead 10 securely fastened to the treatment site. An implantable medical device, such as a defibrillation unit or pacemaker, then may be suitably electrically connected to the proximal end 68 of lead 10.

Figure 5:
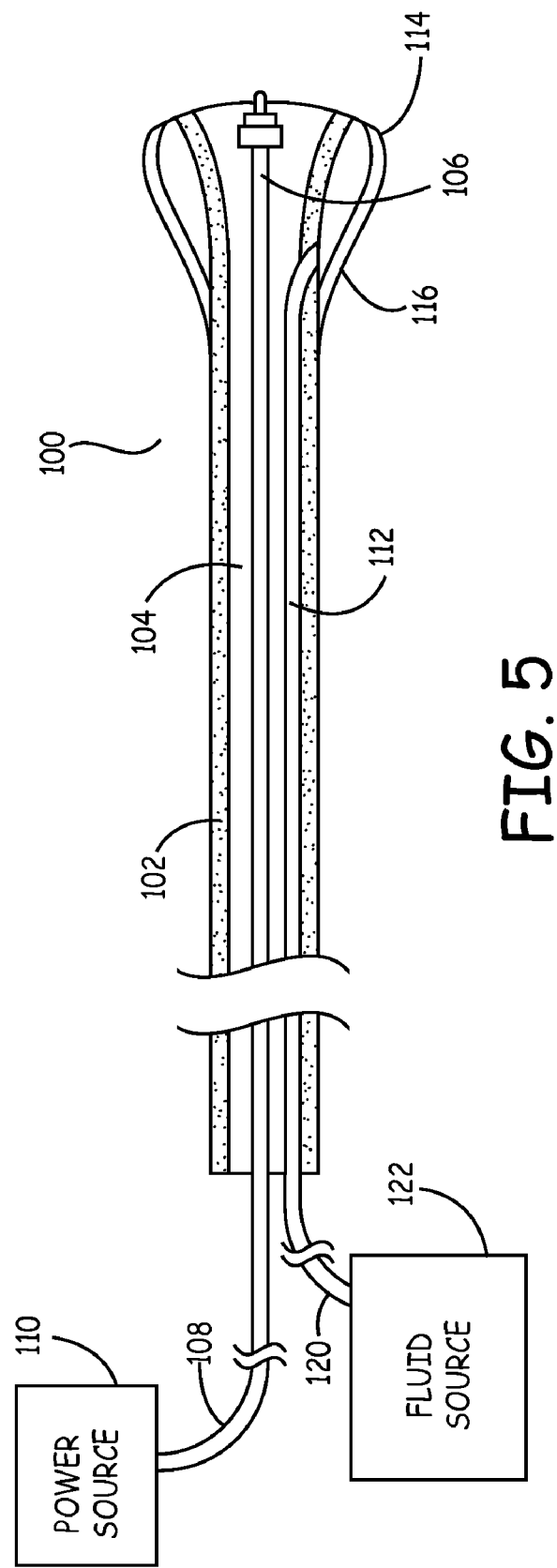
FIG. 5 is a cross-sectional view of the medical lead of FIG. 1 disposed within a balloon catheter.

In a further exemplary embodiment of the invention, delivery catheter 28 may further include a balloon. The balloon can be used to clear the treatment site of undesired blood, water, fluid and/or tissue upon inflation so that the electrode of lead 10 can make suitable contact with the treatment site. It will be appreciated that the balloon catheter may comprise any conventional balloon catheter used in the medical industry. FIG. 5 illustrates a balloon catheter 100 in accordance with one exemplary embodiment of the present invention. Balloon catheter 100 includes a flexible body 102 within which is formed a first lumen 104. First lumen 104 is adapted to receive lead 10, as described above, and permits delivery of lead 10 to a treatment site. Lead 10 includes at a distal end 106 at least one electrode, such as a tip electrode, and may be connected at a proximal end 108 to a power source 110, such as a pacemaker or other implantable medical device. As illustrated in FIG. 5, balloon catheter 100 further includes a fluid lumen 112 through which a fluid, such as air or water, may flow from a fluid source 122 connector to proximal end 120 to balloon 116 that is disposed at a distal end 114 of balloon catheter 100.

In accordance with an exemplary embodiment of the invention, a method for using a balloon catheter to deliver a medical lead to a treatment site and to securely couple an implantable medical device to the treatment site of a heart will be described. For convenience, the method will be described with reference to balloon catheter 100 and medical lead 10. However, it will be understood that the method may utilize any suitable balloon catheter and any suitable embodiment of the medical lead of the present invention. Lead 10 may be secured to a selected treatment site, such as the myocardium of the heart, using balloon catheter 100 by first inserting balloon catheter 100 into a suitable blood vessel and urging balloon catheter 100 through the blood vessel until a distal end of balloon catheter 100 is positioned proximate to the myocardium. Fluid source 122 then may be suitably activated to inflate balloon 116 causing balloon 116 to expand at the treatment site, thus clearing the treatment site of excess fluid and/or tissue. Lead 10 then may be inserted into first lumen 104 and urged through balloon catheter 100 until the electrode is proximate the treatment site. In an alternative embodiment of the invention, lead 10 may be urged through balloon catheter 100 before inflating balloon 116. Fluid source 122 then may be activated before lead 10 is secured to the treatment site to ensure that glue segment 16 makes suitable contact with the tissue (i.e., myocardium) at the treatment site. Lead 10 then may be urged against the treatment site so that glue segment 16 contacts the treatment site and adheres thereto upon contact with moisture at the treatment site once balloon catheter 100 is deflated and removed from the treatment site. An implantable medical device, such as a defibrillation unit or pacemaker, then may be suitably electrically connected to the proximal end 108 of lead 10.

Figure 6:
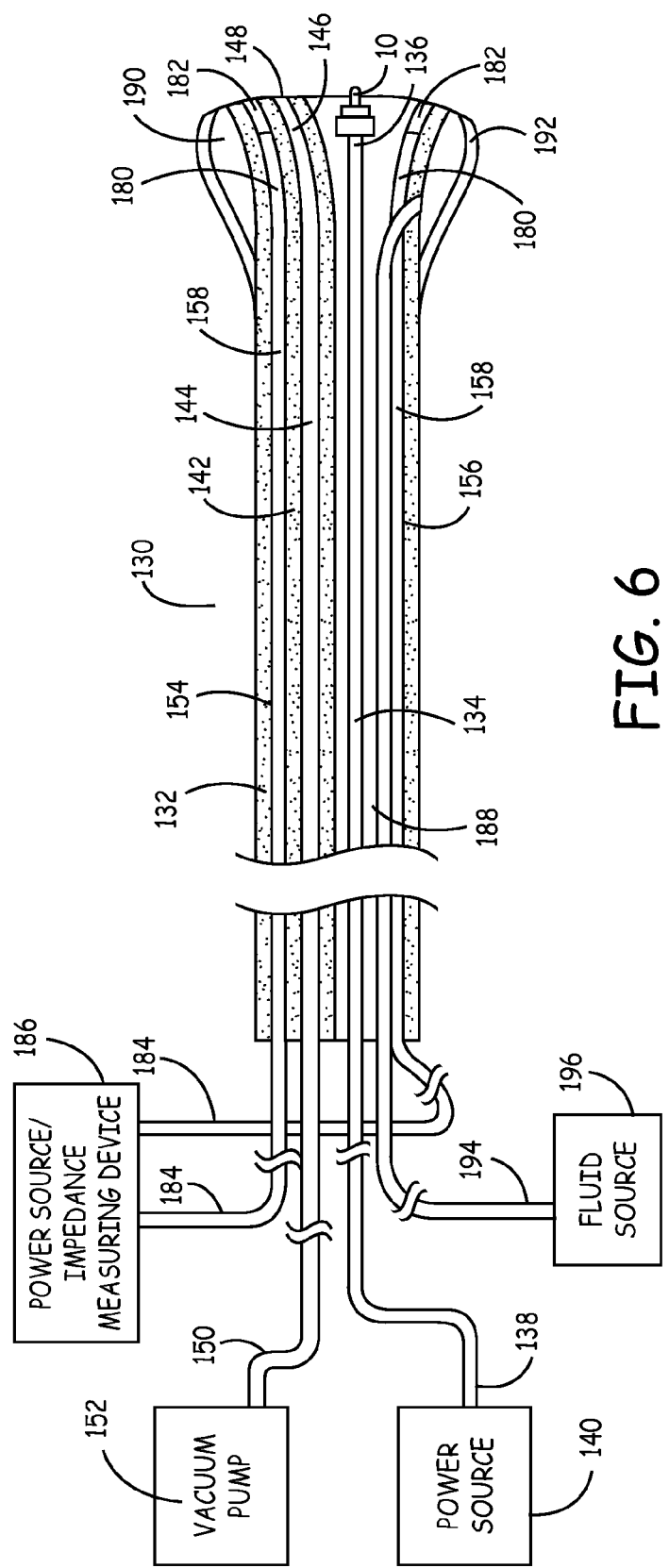
FIG. 6 is a cross-sectional view of the medical lead of FIG. 1 disposed within a delivery catheter having suctioning, mapping and balloon functionality.

In another exemplary embodiment of the invention, delivery catheter 28 includes a combination of mapping, suction and a balloon. FIG. 6 illustrates a delivery catheter 130 in accordance with one exemplary embodiment of the present invention. Delivery catheter 130 includes a flexible body 132 within which is formed a first lumen 134. First lumen 134 is adapted to receive lead 10, as described above, and permits delivery of lead 10 to a treatment site. Lead 10 includes at a distal end 136 at least one electrode, such as a tip electrode, and may be connected at a proximal end 138 to a power source 140, such as a pacemaker or other implantable medical device. Delivery catheter 130 further includes a second lumen 142 within which is seated a suction tube 144. Suction tube 144 has at a distal end 146 an opening 148 for receiving fluid from the treatment site. Suction tube 144 may be connected at a proximal end 150 to a vacuum pump 152 or other suitable device for creating a suction force at opening 148.

Delivery catheter 130 further includes a third lumen 154 and a fourth lumen 156 within which are seated sensors circuits 158. Sensor circuits 158 include at distal ends 180 one or more electrical contacts 182, such as bipolar contacts, through which an electrical current may be emitted and received. Sensors 158 may be connected at proximal ends 184 to a power source/impedance measuring device(s) 186 that is configured to send an electric potential through electrical contacts 182 and measure the change in impedance when electrical contacts 182 contact the treatment site surface. Electrical contacts 182 may be configured to exhibit additional functions. For example, electrical contacts 182 may be configured to sense intrinsic electrical activity of the heart in order to aid in optimizing the location of the treatment site. Delivery catheter 130 further includes a fluid lumen 188 through which a fluid, such as air or water, flows from a fluid source 196 connected to a proximal end 194 to a balloon 190 at a distal end 192 proximate to the distal end of delivery catheter 130.

In accordance with an exemplary embodiment of the invention, a method for using a multi-function delivery catheter to deliver a medical lead to a treatment site and to securely couple an implantable medical device to the treatment site of a heart will be described. For convenience, the method will be described with reference to multi-function delivery catheter 130 and medical lead 10. However, it will be understood that the method may utilize any suitable multi-function delivery catheter and any suitable embodiment of the medical lead of the present invention. Lead 10 may be secured to a selected treatment site, such as the myocardium of the heart, using delivery catheter 130 by first inserting delivery catheter 130 into a suitable blood vessel and urging delivery catheter 130 through the blood vessel until a distal end of delivery catheter 130 is positioned proximate to the myocardium. As delivery catheter 130 is urged through the blood vessel, power source/impedance measuring device 186 may transmit an electric potential through electrical contacts 182 and the impedance between the electrical contacts 182 may be measured by the power source/impedance measuring device 186. When a suitable change in the impedance between the electrical contacts 182 indicates that the distal end of delivery catheter 130 is proximate to the treatment site, lead 10 may be inserted into first lumen 134 and urged through delivery catheter 130 until distal end 136 of lead 10 is proximate the treatment site.

Vacuum pump 152 may be activated so that a suitable amount of fluid at the treatment site is removed through opening 148 of suction tube 144. Fluid source 196 also may be suitably activated to inflate balloon 190 causing balloon 190 to expand at the treatment site, thus clearing the treatment site of further excess fluid and/or tissue. In one embodiment of the present invention, vacuum pump 152 may be activated before fluid source 196. In an alternative embodiment of the invention, fluid source 196 may be activated before activation of vacuum pump 152. In another alternative embodiment of the invention, fluid source and/or vacuum pump 152 may be activated before the distal end of lead 10 is positioned proximate to the treatment site.

After a suitable period of suction time, and/or after a suitable amount of fluid has been removed from the treatment site, and after balloon 190 has been inflated, lead 10 then may be urged against the treatment site so that glue segment 16 contacts the treatment site and adheres thereto, after balloon 190 is deflated and vacuum pump 152 is deactivated, upon contact with moisture at the site. Delivery catheter 130 then may be removed from the treatment site and the blood vessel, leaving lead 10 securely fastened to the treatment site.

Figure 7:
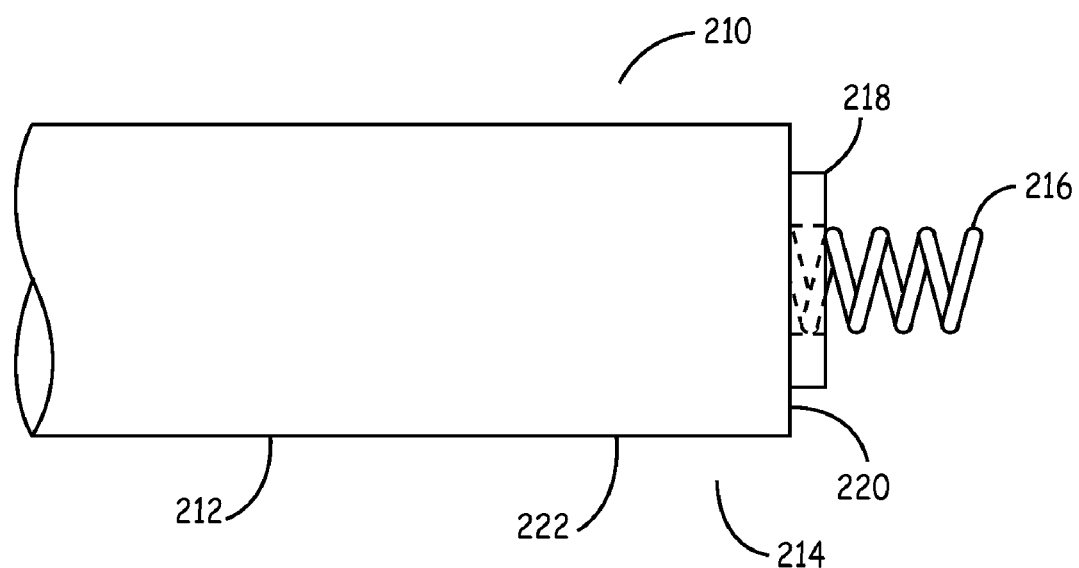
FIG. 7 is a plan view of a portion of a medical lead in accordance with another exemplary embodiment of the present invention.

FIG. 7 is a plan view of a distal portion of a medical electrical lead 210, in accordance with another exemplary embodiment of the present invention. Lead 210 includes an elongated insulative lead body 212 fabricated, for example, of silicone rubber, polyurethane or other biocompatible elastomer. At a distal end 214 of lead 210 is disposed a helix-coil electrode 216, which is coupled to a conductor (not shown) within lead body 212. In this exemplary embodiment of the invention, helix-coil electrode 216 may correspond to any conventionally available epicardial and/or endocardial pacing and/or defibrillation helix-coil electrodes that are configured for affixation to a treatment site.

Lead 210 further includes a glue segment 218 comprising any conventionally available tissue glue, such as, for example, those that form glue segment 16 described above with reference to FIG. 1. In one exemplary embodiment, illustrated in FIG. 7, glue segment 218 has a disc or annular shape with helix-coil electrode 216 positioned in the center of glue segment 218. In another exemplary embodiment, glue segment 218 is formed by one or more "spots" or "dots" of tissue glue positioned proximate to helix-coil electrode 216. Alternatively, glue segment 218 may take on any other shape and size suitable to adhere lead 210 to a tissue or organ.

Glue segment 218 is located near distal end 214 of lead 210 at any suitable point proximate to helix-coil electrode 216. In this manner, as helix-coil electrode 216 is screwed or wound into the treatment site from torque applied to lead 210, glue segment 218 contacts the treatment site. When glue segment 218 has made sufficient contact with the treatment site, glue segment 218 will be cured, such as upon contact with a sufficient amount of moisture at the treatment site, to provide an auxiliary anchoring to helix-coil electrode 216. In an exemplary embodiment of the invention, glue segment 218 is disposed at a distal surface 220 of lead body 212 that is perpendicular to a longitudinal surface 222 of lead body 212.

Figure 8:
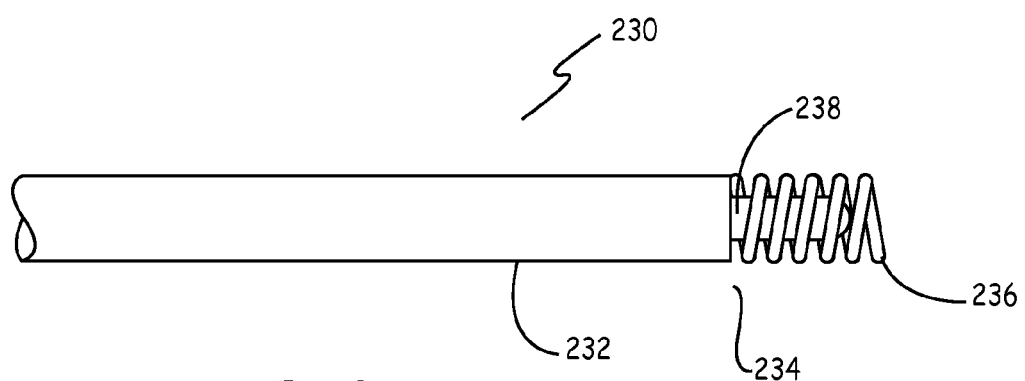
FIG. 8 is a plan view of a portion of a medical lead in accordance with a further exemplary embodiment of the present invention.

FIG. 8 illustrates a lead 230 in accordance with another exemplary embodiment of the invention. Lead 230 includes an elongated insulative lead body 232 fabricated, for example, of silicone rubber, polyurethane or other biocompatible elastomer. At a distal end 234 of lead 230 is disposed a helix-coil electrode 236, which is coupled to a conductor (not shown) within lead body 232. In this exemplary embodiment of the invention, helix-coil electrode 236 may correspond to any conventionally available epicardial and/or endocardial pacing and/or defibrillation helix-coil electrodes that are to be affixed to a treatment site. Lead 230 also has a glue segment 238 that resides within the coiling of helix-coil electrode 236. In one exemplary embodiment, glue segment 238 is formed of a stiff gel which maintains a desired shape, such as an elongated or tubular shape. In this manner, as helix-coil electrode 236 is screwed or wound into the treatment site from torque applied to lead 230, glue segment 238 contacts the treatment site and spreads. Glue segment 238 then will be cured, such as upon contact with a sufficient amount of moisture, to provide auxiliary anchoring to helix-coil electrode 236.

In another exemplary embodiment of the invention, glue segment 238 further includes a capsule encapsulating the tissue glue. Accordingly, as helix-coil electrode 236 advances into the treatment site from torque applied to lead 230, pressure is applied to the capsule, which ruptures and liberates the tissue glue. Again, glue segment 238 then will be cured, such as upon contact with a sufficient amount of moisture. In accordance with this embodiment, glue segment 238 is encapsulated by any suitable method. In one embodiment of the invention, a biodegradable/biocompatible polymer that is formulated to rupture when lead 230 is suitably urged against the treatment site encapsulates glue segment 238. In another exemplary embodiment of the invention, a biocompatible encapsulating material such as fibrin that can rupture when lead 230 is suitably urged against the treatment site encapsulates glue segment 238. In a further exemplary embodiment of the invention, glue segment 238 is encapsulated by partially cured tissue glue. The partially cured tissue glue encapsulant may be suitably partially cured such that it can rupture when lead 230 is urged against the treatment site.

According to yet another embodiment, lead 230 further includes a lumen extending along a length of lead 230 (not shown) through which a segment of glue, for example glue segment 238, may be delivered. Once helix-coil electrode 236 has been wound into the tissue of the treatment site to a desired extent, tissue glue 238 may be advanced through the lumen of lead 230 until a suitable amount of tissue glue exits distal end 234 of lead 230 and is applied to the treatment site.

According to another aspect of the present invention a suitable solvent is used to remove lead 230, or any of the previously described leads, from the treatment site. According to one embodiment, once the implantable medical device is disconnected from the proximal end of lead 230, the proximal end of lead 230 may be inserted into the lumen of a catheter, such as catheter 28 illustrated in FIG. 2, having a suctioning function. The catheter then may be advanced along lead 230 until the distal end of the catheter is proximate to the cured tissue glue. A suitable solvent, such as DMSO or acetone, then may be advanced through a lumen of the catheter to the cured tissue glue. As the tissue glue disassociates and/or dissolves, the catheter may aspirate the glue residue and debris from the body. Once the tissue glue has sufficiently dissolved, lead 230 may be removed from the treatment site, such as by "unscrewing" electrode 236 from the tissue, and lead 230 and the catheter may be suitably removed from the treatment site.

While exemplary embodiments have been presented in the foregoing detailed description, it should be appreciated that a vast number of variations exist. For example, while the present invention has been described with reference to the use of medical electrical leads having electrodes that monitor or treat a heart, it will be appreciated that the present invention may be used to couple to any organ or tissue any suitable medical lead. Further, while the implantable medical device has been described as a defibrillation unit or pacemaker, the implantable medical device may be any medical device suitable for monitoring or treating tissue or an organ. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. A medical lead, comprising:

an elongated lead body having a longitudinal axis and terminating in a distal end surface;

a tip electrode extending outward from the distal end surface of the lead body in a direction that is substantially aligned with the longitudinal axis of the elongated lead body; and a glue segment extending outward from the distal end surface of the lead body in a direction that is substantially aligned with the longitudinal axis of the elongated lead body and disposed within said tip electrode to affix said electrode to a treatment site, wherein the glue segment is encapsulated within a biocompatible capsule.

2. The medical lead of claim 1, wherein said glue segment is a tissue adhesive comprising n-butyl cyanoacrylate.

3. The medical lead of claim 1, wherein said glue segment is a tissue adhesive comprising a fibrin glue.

4. The medical lead of claim 1, wherein said glue segment is formed in a tubular shape.

5. The medical lead of claim 1, wherein said tip electrode is formed from a helix-coil.

6. A system for affixing a medical lead to a tissue site, the system comprising:

a medical lead including a lead body of a first diameter and a tip electrode formed from a helix-coil;

a delivery catheter having a catheter lumen of a second diameter that is larger than said first diameter of the lead body and adapted to receive said medical lead therein and to permit said medical lead to be advanced therethrough;

a glue segment disposed at a distal end of said lead, the glue segment comprising a tissue adhesive adapted to affix said medical lead to the tissue; and a guard disposed about said lead body being proximal to and in proximity to said glue segment, said guard being of a third diameter that is larger than said first diameter of the lead body and smaller than said second diameter of the delivery catheter lumen, said guard projecting outward from said lead body to prevent said glue segment from contacting a wall of said delivery catheter lumen as said lead is advanced therethrough.

7. The system of claim 6, wherein said tissue adhesive comprises a n-butyl cyanoacrylate.

8. The system of claim 6, wherein said tissue adhesive comprises a fibrin glue.

9. The system of claim 6, wherein said glue segment is formed in an annular shape.

10. The system of claim 6, wherein said glue segment is formed in a tubular shape.

11. The system of claim 6, wherein said glue segment includes dots of tissue adhesive.

12. The system of claim 6, wherein said tissue adhesive is disposed about said tip electrode.

13. The system of claim 6, wherein said catheter includes a balloon disposed at a distal end of said catheter and adapted to clear said tissue site.

14. The system of claim 6, wherein said catheter is adapted to apply suction in proximity to said tissue site.

15. The system of claim 6, wherein said catheter includes mapping electrodes.

16. The system of claim 6, further comprising an implantable medical device adapted for coupling to said medical lead.

17. A system for affixing a medical lead to a tissue site, the system comprising:

a medical lead including a lead body of a first diameter and a tip electrode formed from a helix-coil;

a delivery catheter having a catheter lumen of a second diameter that is larger than said first diameter of the lead body and adapted to receive said medical lead therein and to permit said medical lead to be advanced therethrough;

a glue segment disposed at a distal end of said lead, the glue segment comprising an unencapsulated tissue adhesive adapted to affix said medical lead to the tissue; and a guard disposed about said lead body being proximal to and in proximity to said glue segment, said guard being of a third diameter that is larger than said first diameter of the lead body and smaller than said second diameter of the delivery catheter lumen, said guard projecting outward from said lead body to prevent said glue segment from contacting a wall of said delivery catheter lumen as said lead is advanced therethrough.

* * * * *